United States Patent [19]

Zeelen

[11] 4,330,540
[45] May 18, 1982

[54] ENT-16-AMINO-17-HYDROXY-OESTRA-1,3,5(10)-TRIENES AND DERIVATIVES THEREOF, AND PHARMACEUTICAL COMPOSITIONS

[75] Inventor: Filippus J. Zeelen, Heesch, Netherlands

[73] Assignee: Akzo N.V., Oss, Netherlands

[21] Appl. No.: 230,043

[22] Filed: Jan. 29, 1981

[51] Int. Cl.$^3$ .................. A01N 45/00; C07J 1/00
[52] U.S. Cl. .................. 424/238; 260/397.5
[58] Field of Search ...................... 260/397.5

[56] References Cited

U.S. PATENT DOCUMENTS 3,440,243  4/1969  Schaub et al. ............... 260/239.55

Primary Examiner—Elbert L. Roberts
Attorney, Agent, or Firm—Abelman, Frayne & Rezac

[57] ABSTRACT

New and pharmacologically useful ent-16-amino-17-hydroxy-oestra-1,3,5(10)-trienes are disclosed having the formula I:

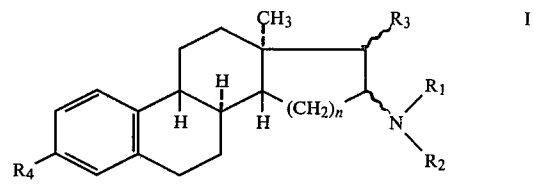

and pharmaceutically acceptable non-toxic acid addition salts thereof, wherein:

n = 1 or 2, preferably 1

$R_1$ = H or hydrocarbyl of 1 to 6 carbon atoms (preferably lower alkyl, such as methyl);

$R_2$ = H or hydrocarbyl of 1 to 6 carbon atoms (preferably lower alkyl, such as methyl); or $R_1$ and $R_2$ together is alkylene of 4 or 5 carbon atoms;

$R_3$ = a free, esterified or etherified hydroxyl group; and $R_4$ = a free, esterified or etherified hydroxyl group.

The novel compounds have antiarrhythmic properties.

8 Claims, No Drawings

ENT-16-AMINO-17-HYDROXY-OESTRA-1,3,5(10)-TRIENES AND DERIVATIVES THEREOF, AND PHARMACEUTICAL COMPOSITIONS

This invention relates to novel ent-16-amino-17-hydroxy-oestra-1,3,5(10)-trienes and derivatives thereof, and to pharmaceutical compositions containing these compounds as active component.

It is generally believed that enantiomeric steroids (ent-steroids) are biologically inactive. Only a few examples are known from literature wherein ent-steroids show some activity though negligible in comparison with the activity of the corresponding natural isomer.

Surprisingly, it was found that novel ent-steroids of the oestra-1,3,5(10)-triene-series, substituted in 16-position with a primary, secondary or tertiary amino group and in 17-position with a free, esterified or etherified hydroxyl group, are potent anti-arrhythmic agents.

Therefore, the present invention relates to novel ent-oestra-1,3,5(10)-trienes having the formula I:

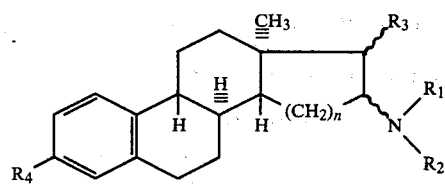

and pharmaceutically acceptable non-toxic acid addition salts thereof, wherein:

$n = 1$ or 2, preferably 1

$R_1 = H$ or hydrocarbyl of 1 to 6 carbon atoms (preferably lower alkyl, such as methyl);

$R_2 = H$ or hydrocarbyl of 1 to 6 carbon atoms (preferably lower alkyl, such as methyl); or $R_1$ and $R_2$ together is alkylene of 4 or 5 carbon atoms;

$R_3 =$ a free, esterified or etherified hydroxyl group; and $R_4 =$ a free, esterified or etherified hydroxyl group.

The invention also relates to pharmaceutical compositions containing a pharmaceutically effective amount of one or more of the novel compounds indicated hereinbefore.

A special group of compounds is the group having formula II:

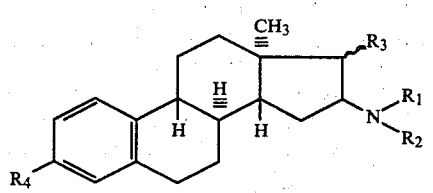

and pharmaceutically acceptable non-toxic acid addition salts thereof, wherein $R_1$, $R_2$, $R_3$ and $R_4$ have the meanings given hereinbefore and $R_3$ is preferably in $\beta$-position.

The novel compounds have antiarrhythmic properties, have no or minimal and transient haemodynamic effects, and do not cause CNS-stimulation in the dosages required. They also have prophylactic effect and decrease infarctsize.

The compounds according to the invention can be prepared by methods employing steps known or obvious to those skilled in the art.

The methods generally comprise the use of ent-oestrone (1-oestrone) or the methylether thereof; ent-oestrone is known in the art and can be prepared by total synthesis using e.g. the method according to Torgov or the method according to Johnson. See for example "Total Steroid Synthesis" by A. A. Akhrem and Y. A. Titov., Plenum Press, 1970, and J.A.C.S. 95, 7501 (1973). When total synthesis leads to racemic oestrone (dl-oestrone), the racemate can be resolved in the usual way, e.g. by reaction with an optically active acid, fractional crystallization or chromatography of the ester formed and hydrolysis, to give the 1-isomer (ent-oestrone).

ent-Oestrone is first enolacylated, e.g. by reacting the 17-ketone with an isopropenyl acylate, such as isopropenyl acetate, in the presence of an acid catalyst such as sulphuric acid, to give the $\Delta^{16}$-17-acylate, which is then reacted with bromine to the ent-16α-bromo-17-ketone. The ent-16α-bromo-17-ketone can also be prepared from ent-oestrone by reacting ent-oestrone with lithium-di-isopropylamide to give the $\Delta^{16}$-17-lithium-enolate which is readily converted with bromine to the ent-16α-bromo-17-ketone.

The ent-16α-bromo-17-ketone is epimerized to the corresponding ent-16β-bromo-17-ketone with potassium bromide in dimethylformamide. The 17-oxo group is then reduced with a complex metal hydride, e.g. sodiumborohydride, to the 17β-hydroxy group. Reaction of the ent-16β-bromo-17β-hydroxy compound with an alkali metal azide, e.g. sodium azide, in dimethylsulphoxide affords the ent-16α-azido-17β-ol, which on reduction with a complex metal hydride, e.g. lithiumaluminiumhydride gives the ent-16α-amino-17β-ol. Another method is analogous to that described in Pharmazie 30 (1975), pp. 32 to 34, which is incorporated herein by reference. See also British Pat. No. 1 359 263.

The intermediate ent-16α-azido-17β-ol can be oxidized, e.g. with Jones reagent (chromic acid), to the ent-16α-azido-17-ketone which on reduction with an alkalimetal borohydride, e.g. lithium borohydride, gives the ent-16α-azido-17α-ol. Further reduction with lithiumaluminiumhydride affords the ent-16α-amino-17α-ol.

The four epimeric ent-16-amino-17-ols can also be prepared as described in Tetrahedron 31 (1975), pp. 1113 to 1118, (which is incorporated herein by reference) starting from the ent-16, 17-epoxides.

Reaction of the ent-16α, 17α-epoxy-oestra-1,3,5(10)-triene compound with methylamine, dimethylamine, isopropylamine, t-butylamine, pyrrolidine, piperidine, respectively, gives the corresponding ent-16β-aminated-17α-ol. An oxidation-reduction sequence performed on the ent-16β-amino-17α-ol affords the ent-16β-amino-17β-ol. The oxidation-reduction sequence can be performed with Jones reagent or with pyridinium chlorochromate for converting the 17α-ol into the 17-ketone, followed by reduction of the 17-ketone with an alkalimetalborohydride, e.g. $NaBH_4$ to the 17β-ol.

The ent-16α, 17α-epoxide can be prepared from ent-oestrone by reaction with hydrazine sulphonate, e.g. hydrazine-tosylate to give the 17-tosylhydrazone, reaction of the 17-tosylhydrazone with methyllithium to afford the $\Delta^{16}$ compound and finally conversion of the $\Delta^{16}$ compound with a peracid, e.g. peracetic acid or perphtalic acid, in a suitable solvent such as acetic acid/chloroform, into the ent-16α, 17α-epoxide.

When the ent-16α, 17α-epoxide is reacted with aqueous sodiumazide in dimethylacetamide the ent-16β-azido-17α-ol is formed, which on reduction with lithiumaluminiumhydride gives the ent-16β-amino-17α-ol.

The ent-16β-azido-17α-ol can be converted into the ent-16β-azido-17β-ol with the oxidation-reduction sequence as described hereinbefore, whereafter reduction with lithiumaluminiumhydride affords the ent-16β-amino-17β-ol.

An ent-16-methylamino compound can readily be prepared from the corresponding ent-16-amino compound by N-formylation, e.g. by reacting with ethylformate in ethanol in the presence of sodium ethoxide, followed by reduction of the 17-formamido steroid thus-obtained, e.g. with a complex metal hydride, preferably with lithiumaluminiumhydride in tetrahydrofuran.

An ent-16-dimethylamino compound can be obtained by repeating the above N-formylation and reduction on an ent-16-methylamino compound. Also, direct conversion of an ent-16-amino or an ent-16-methylamino compound into an ent-16-dimethylamino compound is possible by methylation with formic acid/formalin.

An ent-16-isopropylamino compound can be prepared by heating an ent-17α-hydroxy-16β-amino compound with acetone at reflux temperature, affording the intermediate ent-16-isopropylidene-imino compound which can be reduced with a complex metal hydride to the desired ent-16β-isopropylamino-17α-hydroxy compound. Another route to this ent-16β-isopropylamino compound is the alkylation of an ent-17α-hydroxy-16β-amine with isopropyliodide in a suitable solvent, such as dimethylformamide, in the presence of sodium methoxide.

The substituents in position 3 may be present in the starting substances or may be introduced after the introduction of the vicinal amino-hydroxy substituents in ring D.

In all methods for preparing the novel enantiomeric steroids any hydroxy group in position 3 and/or 17 (if present), and the (alkyl)amino group in position 16 are temporarily protected, if required, by reversible ester- or ether-formation (hydroxy group), or reversible acyl-, or salt-formation (amino group).

Acylation of an ent-16-(alkyl)amino-17-ol provides the ent-16-acyl(alkyl)amino-17-acetate, which on selective alkaline hydrolysis gives the ent-16-acyl(alkyl)amino-17-ol. An 16-acyl(alkyl)amino-17-ol can be hydrolyzed with alkali to the 16-(alkyl)amino-17-ol.

A hydroxy group may be acylated according to procedures well-known in the art, e.g. by reaction with an organic carboxylic acid or a functional derivative thereof, such as the anhydride or the acid chloride, in the presence of a water-binding agent or a base, such as pyridine.

Acyl groups, if present in the 3- and/or 17-position or in the amino group may be hydrolyzed, e.g. with alkali to give the free hydroxy or amino group.

An acyl group, if present in 3- and 17-position, may be derived from an aliphatic, cycloaliphatic, aromatic or araliphatic carboxylic acid with 1-8 carbon atoms, such as acetic acid, propionic acid, pentanoic acid, trimethyl-acetic acid, heptanoic acid, decanoic acid, dodecanoic acid, benzoic acid, β-phenyl propionic acid, cyclo-octyl acetic acid, succinic acid, and the like.

A hydroxy group, if present in the 3- and/or 17-position may be converted into an ether group derived from an aliphatic, aromatic, araliphatic or heterocyclic hydrocarbon, such as the methyl, ethyl, butyl, cyclopentyl, cyclohexyl, tetrahydropyranyl ether group, and the like, according to well-known procedures.

An ether group in 3-position, if present, can be hydrolyzed to the phenol group under acid addition, e.g. by heating with aqueous hydrobromic acid (48%).

An ether group used for protection, such as for example a tetrahydropyranyl-ether group in 17-position, can also be split up under acid conditions.

The preparation of the acid-addition salts of the ent-16-amino compounds of the invention can be performed by treatment of the amino compound with an inorganic acid such as hydrochloric acid, hydrobromic acid, phosphoric acid, nitric acid, or an organic acid, such as citric acid, pyruvic acid, succinic acid, maleic acid, sulphonic acids.

The new compounds according to the invention may be used in the form of pharmaceutical compositions, for which purpose they are mixed with one or more pharmaceutically acceptable non-toxic carriers and/or the usual excipients suitable for enteral, i.e. oral, administration or for parenteral administration, e.g. for injection.

The effective oral dose is in the range from 0.5–25 mg/kg and the effective intravenous dose is in the range from 0.1–10 mg/kg.

The following examples illustrate the invention.

EXAMPLE I (a) ent-17-Acetoxy-3-methoxyoestra-1,3,5(10), 16-tetraene

A mixture of ent-oestrone methyl ether (20.0 g), isopropenyl acetate (160 ml) and a trace of sulphuric acid (~0.1 ml) was refluxed for 2 hours. The reaction mixture was distilled slowly until 40 ml of liquid had been collected. Fresh isopropenyl acetate (40 ml) and a trace of sulphuric acid (~0.1 ml) were added to the reaction mixture, which again was distilled very slowly until 40 ml of liquid had been collected. This procedure was repeated once more. The reaction mixture was cooled to 40° C., mixed with anhydrous sodium acetate (6 g) and poured into water. The resulting mixture was extracted with ether. The extracts were washed neutral with water, dried over anhydrous $Na_2SO_4$ and concentrated in vacuo. The residue was dissolved in cyclohexane/ethylacetate 9:1 and filtered over alumina (activity III). Concentration gave 21.4 g of product, m.p. 97°–100° C., $[\alpha]_D^{20} = -95.2°$ (C=1, $CHCl_3$).

(b) ent-16α-Bromo-3-methoxyoestra-1,3,5(10)-trien-17-one

A mixture of ent-17-acetoxy-3-methoxy-oestra-1,3,5(10), 16-tetraene (21.4 g), powdered anhydrous potassium carbonate (25 g) and dry carbon tetrachloride (1.3 l) was cooled to 0° C. with vigorous stirring a solution of bromine (4.2 ml, 13.3 g) in dry carbon tetrachloride (370 ml) was added rapidly (in ca. 5 min.). The reaction mixture was immediately poured into 3% aqueous sodium thiosulphate (1.0 l). The organic layer was dried over anhydrous potassium carbonate and concentrated in vacuo. The residue was recrystallized from methanol/dichloormethane to give 17.4 g of pure product, m.p. 146°–149° C., $[\alpha]_D^{20} = -119°$ (C=1, $CHCl_3$).

(c) ent-16β-Bromo-3-methoxyoestra-1,3,5(10)-trien-17β-ol

A mixture of ent-16α-bromo-3-methoxyoestra-1,3,5(10)-trien-17-one (11.0 g), powdered anhydrous potassium bromide (13.0 g) and dry dimethyl formamide (220 ml) was heated at 85° C. with stirring for 2 hours. The reaction mixture was cooled, diluted with water and extracted with ethyl acetate. The extracts were dried over anhydrous Na$_2$SO$_4$ and concentrated in vacuo. The residue was suspended in methanol (500 ml) and treated at −4° C. with a 1% solution of NaOH in methanol (50 ml). Sodium borohydride (2.42 g) was added in small portions with stirring and the resulting mixture was stirred for an additional hour at −4° C. Water (800 ml) was added and after one hour the precipitated product was collected, dried and recrystalized from dichloromethane/methanol. Thus 9.1 g product was obtained, m.p. 101°–103° C., $[\alpha]_D^{20} = -50.6°$ (C=2, CHCl$_3$).

(d)

ent-16α-Azido-3-methoxyoestra-1,3,5(10)-trien-17β-ol

A mixture of ent-16β-bromo-3-methoxyoestra-1,3,5(10)-trien-17β-ol (9.1 g), anhydrous sodium azide (5.4 g) and dry dimethyl sulphoxide (90 ml) was heated with stirring at 90° C. for 1 hour. The reaction mixture was cooled, diluted with water and extracted with ether. The extracts were dried over anhydrous Na$_2$SO$_4$ and concentrated in vacuo. The residue was crystallized from dichloromethane/hexane to give 6.6 g of product, m.p. 109°–112° C., $[\alpha]_D^{20} = -16°$ (C=1, CHCl$_3$).

(e)

ent-16α-amino-3-methoxyoestra-1,3,5(10-trien-17β-ol and its hydrochloride

A solution of ent-16α-azido-3-methoxyoestra-1,3,5(10)-trien-17β-ol (6.6 g) in dry tetrahydrofuran (260 ml) was cooled to 5° C. under an atmosphere of dry nitrogen. Lithium aluminium hydride (3.8 g) was added in portions with stirring. The resulting mixture was refluxed for one hour and then cooled in an ice bath. With stirring 40% aqueous KOH (300 ml) was added slowly. The organic layer was separated, dried over anhydrous K$_2$CO$_3$ and concentrated in vacuo. The residue was suspended in ether (100 ml) and allowed to reflux for 20 min. The mixture was cooled in ice for 2 hours and the precipitated product was collected by filtration; yield 5.3 g ent-16α-amino-3-methoxyoestra-1,3,5(10)-trien-17β-ol, m.p. 159°–161° C., $[\alpha]_D^{20} = -40°$ (C=1, pyridine).

A solution of the amine (3.1 g) in dry methanol (100 ml) was saturated with hydrogen chloride at room temperature. Precipitation of the hydrochloride was completed by concentration of the reaction mixture to ca. 25 ml and addition of dry ether. Filtration gave 3.3 g of the hydrochloride, m.p. >300° C. $[\alpha]_D^{20} = -55°$ (C=1, dimethylsulphoxide).

EXAMPLE II (a)

ent-16α-formamido-3-methoxyoestra-1,3,5(10)-trien-17β-ol

To a suspension of ent-16α-amino-3-methoxyoestra-1,3,5(10)-trien-17β-ol (5.3 g) in a mixture of ethyl formate (60 ml) and absolute ethanol (30 ml) was added sodium (0.40 g) cut into small pieces. The resulting suspension was stirred under nitrogen at room temperature for 2 hours. Then the mixture was poured into ice water (600 ml) and volatile components were removed in vacuo. The precipitated product was collected by filtration, washed with water and dried in vacuo. Thus 5.4 g of colourless product was obtained, which was used in the next step without purification.

(b)

ent-3-methoxy-16α-methylamino-oestra-1,3,5(10)-trien-17β-ol and its hydrochloride Lithium aluminium hydride (2.5 g) was added in portions to a stirred suspension of ent-16α-formamido-3-methoxyoestra-1,3,5(10)-trien-17β-ol (5.4 g) in dry tetrahydrofuran (200 ml). The resulting mixture was allowed to reflux for 2.5 hours and then cooled in an ice bath. The excess of hydride was destroyed by careful addition of saturated aqueous Na$_2$SO$_4$. The resulting mixture was heated to 50° C. and the precipitated salts removed by filtration of the hot suspension. The filter cake was washed thoroughly with dichloromethane/tetrahydrofuran 1:1. The combined filtrates were concentrated in vacuo and the residue was crystallized from ether to give 4.64 g of the title amino-alcohol, m.p. 162°–164° C., $[\alpha]_D^{20} = -21.6°$ (C=1, pyridine).

This product was dissolved in a mixture of dichloromethane (40 ml) and methanol (5 ml). Hydrogen chloride gas was bubbled through the solution for 10 min. The resulting precipitate was collected by filtration and washed with ether. This gave 5.0 g of the hydrochloride, m.p.>275° C., $[\alpha]_D^{20} = -46.0°$ (C=1, in dimethylsulphoxide).

EXAMPLE III ent-16α-i-propylamino-3-methoxyoestra-1,3,5(10)-trien-17β-ol and its hydrochloride A mixture of ent-16α-amino-3-methoxyoestra-1,3,5(10)-trien-17β-ol hydrochloride (3.26 g), 4 A molecular sieves (10.0 g), absolute methanol (20 ml) and acetone (10 ml) was stirred at room temperature, for 48 hours. Subsequently sodium cyanoborohydride (0.63 g) was added in portions and the resulting mixture was stirred at room temperature for 3 hours. The reaction mixture was rendered alkaline with aqueous 2 N NaOH, diluted with dichloromethane and filtered. The organic layer was washed with water, dried over anhydrous Na$_2$SO$_4$ and concentrated in vacuo. The residue was crystallized from ether to give 2.5 g of the title amino-alcohol, m.p. 128°–132° C., $[\alpha]_D^{20} = -26.6°$ (C=1, CHCl$_3$).

This product was treated with hydrogen chloride in methanol. Upon addition of ether the hydrochloride precipitated and was collected by filtration, 2.7 g, m.p. >250° C., $[\alpha]_D^{22} = -57.3°$ (C=1, DMSO).

EXAMPLE IV ent-16α-amino-oestra-1,3,5(10)-triene-3,17β-diol

A solution of ent-16α-amino-3-methoxyoestra-1,3,5(10)-trien-17β-ol (1.4 g) in aqueous 48% HBr (80 ml) was heated at 100° C. for 2.5 hours. The reaction mixture was diluted with water and rendered slightly alkaline by addition of solid K$_2$CO$_3$ in small portions (foaming!).

The resulting mixture was extracted with dichloromethane/tetrahydrofuran 2:1. The extracts were dried over anhydrous Na$_2$SO$_4$ and concentrated in vacuo. The residue was triturated with ether (100 ml), which gave the title amino-alcohol in crystalline form, 1.1 g, m.p. 250°–255° C., $[\alpha]_D^{20} = -34°$ (C=1, pyridine).

EXAMPLE V ent-16α-Amino-oestra-1,3,5(10)-triene-3,17β-diol maleate (salt)

ent-16α-Amino-oestra-1,3,5(10)-triene-3,17β-diol (30 g) was dissolved in methanol (3 l) and the solution was filtered to remove extraneous matter. Maleic acid (12 g) in methanol (200 ml) was added and the resulting solution was concentrated to low volume under reduced pressure. The resulting solution was refluxed with charcoal (5 g), filtered through a decalite pad and further reduced in volume. The addition of ether afforded pure ent-16α-amino-oestra-1,3,5(10)-triene-3,17β-diol maleate (1:1) (salt) (30 g), m.p.>200° C. (decomp.), $[\alpha]_D^{20} = -45°$ (C 0.9 in dimethylsulphoxide).

EXAMPLE VI ent-16α-Methylamino-oestra-1,3,5(10)-triene-3,17β-diol maleate (salt)

In a similar way as described in Example V ent-16α-methylamino-oestra-1,3,5(10)-triene-3,17β-diol was converted into its maleate salt, m.p.>200° C. (decomp.), $[\alpha]_D^{20} = -40°$ (C 1.2 in dimethylsulphoxide).

EXAMPLE VII (a)

ent-16α-(N-formyl-N-methylamino)-oestra-1,3,5(10)-triene-3,17β-diol 3-methylether Sodium (1.91 g) was added portionwise to a suspension of ent-16α-methylamino-oestra-1,3,5(10)-triene-3,17β-diol 3-methylether (6.0 g) in ethylformate (60 ml) and ethanol (30 ml). The resultant solution was stirred for 2 h., when methanol was added to dissolve the precipitated sodium salt. The solution was acidified with 5 N hydrochloric acid and water (500 ml) was added to precipitate the crude product, which was filtered off and washed with water. Crystallisation from dichloromethane-methanol afforded ent-16α-(N-formyl-N-methylamino)-oestra-1,3,5(10)-triene-3,16α-diol (5.4 g).

(b)

ent-16α-Dimethylamino-oestra-1,3,5(10)-triene-3,17β-diol 3-methylether and its hydrochloride A suspension of ent-16α-(N-formyl-N-methylamino)-oestra-1,3,5(10)-triene-3,17β-diol 3-methylether (5.4 g) in tetrahydrofuran (110 ml) was kept at 10° C., while lithiumaluminiumhydride (5.41 g) was added portionwise. The resultant mixture was refluxed for 5 h., then the excess of lithiumaluminiumhydride was destroyed by careful addition of water. The mixture was diluted with a 1:1 mixture of tetrahydrofuran-ethylacetate (500 ml) and refluxed for 3 h. The inorganic salts were filtered off and washed with tetrahydrofuran-ethylacetate (500 ml; 1:1) and the filtrate was evaporated to dryness. The resultant crude product was crystallised from dichloromethane-methanol to give pure ent-16α-dimethylamino-oestra-1,3,5(10)-triene-3,17β-diol 3-methylether (3.8 g); m.p. 147°-150° C., $[\alpha]_D^{20} = -31°$ (C 1.0 in chloroform).

Saturation of a solution of the dimethylamine (3.8 g) in dry methanol with hydrogen chloride and ether-precipitation gave 4.1 g of the hydrochloride, m.p.>260° C. (dec.), $[\alpha]_D^{20} = -57°$ (C 1.3 in chloroform).

EXAMPLE VIII ent-16α-Methylamino-3-methoxy-oestra-1,3,5(10)-trien-17α-ol

Jones oxidation of ent-16α-azido-3-methoxy-oestra-1,3,5(10)-trien-17β-ol gave the corresponding ent-16α-azido-17-one, which on reduction with lithiumborohydride affords ent-16α-azido-3-methoxy-oestra-1,3,5(10)-trien-17α-ol.

In a similar way as described in Example I (e) the ent-16α-azido-17α-ol was converted into ent-16α-amino-3-methoxy-oestra-1,3,5(10)-trien-17α-ol. In a similar way as described in Example II the ent-16α-amino-17α-ol was converted into the title compound, m.p. 269°-278° C.

EXAMPLE IX (a)

ent-16β-Methylamino-3-methoxy-oestra-1,3,5(10)-trien-17α-ol maleate (1:1) (salt)

ent-3-Methoxy-16α,17α-epoxy-oestra-1,3,5(10)-trien was reacted with aqueous methylamine under pressure to afford ent-16β-methylamino-3-methoxy-oestra-1,3,5(10)-trien-17α-ol, which according to method as described in Example V was converted into its maleate salt, m.p. 225°-235° C. (dec.), $[\alpha]_D^{20} = +12°$ (C=1.0 in dimethylsulphoxide).

(b)

ent-16β-Methylamino-oestra-1,3,5(10)-triene-3,17α-diol maleate (1:1) (salt)

In a similar way as described in Example IV ent-16β-methylamino-3-methoxy-oestra-1,3,5(10) trien-17α-ol was hydrolyzed to the corresponding 3,17α-diol, which according to the method as described in Example V was converted into its maleate salt, m.p. 172°-176° C., $[\alpha]_D^{20} = -50°$ (C=1.0 in methanol).

EXAMPLE X ent-16β-Methylamino-3-methoxy-oestra-1,3,5(10)trien-17β-ol maleate (1:1) (salt) and the corresponding 3-hydroxy compound ent-16β-Methylamino-3-methoxy-oestra-1,3,5(10)-trien-17α-ol (in the form of its 16β-methylacetamide) was subjected to Jones oxidation and the 17-ketone thus obtained to reduction with sodiumborohydride affording the 17α-ol, which on hydrolysis gave ent-16β-methylamino-3-methoxy-oestra-1,3,5(10)-trien-17β-ol. Reaction with maleic acid according to Example V gave the maleate salt, m.p. 201°-206° C., $[\alpha]_D^{20} = -46°$ (C=0.9 in dimethylsulphoxide).

In a similar way ent-16β-methylamino-oestra-1,3,5(10)-triene-3,17α-diol was converted into ent-16β-methylamino-oestra-1,3,5(10)-triene-3,17β-diol maleate, m.p. 202°-206° C. $[\alpha]_D^{20} = -57°$ (C=1.0 in methanol).

EXAMPLE XI (a)

ent-16β-amino-3-methoxy-oestra-1,3,5(10)-trien-17α-ol maleate (1:1) (salt)

ent-3-methoxy-16α,17α-epoxy-oestra-1,3,5(10)-triene was treated with aqueous sodiumazide in dimethylacetamide, affording ent-16β-azido-3-methoxy-oestra-1,3,5(10)-trien-17α-ol which on reduction with lithiumaluminiumhydride gave ent-16β-amino-3-methoxy-oestra-1,3,5(10)-trien-17α-ol. Salt formation as in Example V afforded the maleate, m.p. 208°–209° C., $[\alpha]_D^{20} = -49.6°$ (C=0.8 in dimethylsulphoxide).

(b) ent-16β-amino-oestra-1,3,5(10)-triene-3,17α-diol maleate (1:1) (salt)

In a similar way as described in Example IV ent-16β-amino-3-methoxy-oestra-1,3,5(10)-trien-17α-ol was hydrolyzed to the corresponding 3,17α-diol, which according to the method as described in Example V gave the maleate salt, m.p. >200° C. (dec.), $[\alpha]_D^{20} = -55°$ (C=1.0 in methanol).

EXAMPLE XII ent-16β-Amino-3-methoxy-oestra-1,3,5(10)-trien-17β-ol maleate (1:1) (salt)

ent-16β-Azido-3-methoxy-oestra-1,3,5(10)-trien-17α-ol was subjected to an oxidation-reduction sequence with pyridiniumchlorochromate and sodiumborohydride affording the corresponding 17β-ol, which on reduction with lithiumaluminiumhydride gave ent-16β-amino-3-methoxy-oestra-1,3,5(10)-trien-17β-ol. Conversion with maleic acid gave the maleate, m.p. 190°–193° C., $[\alpha]_D^{20} = -51°$ (C=0.8 in dimethylsulphoxide).

I claim:

1. A compound selected from the group consisting of an ent-16-amino-17-hydroxy-oestra-1,3,5(10)-triene having the formula I:

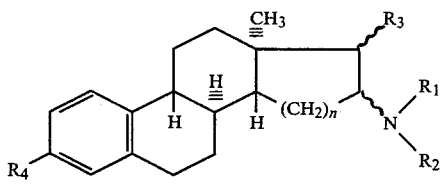

and pharmaceutically acceptable non-toxic acid addition salts thereof, wherein:

n=1;
R₁=H or hydrocarbyl of 1 to 6 carbon atoms;
R₂=H or hydrocarbyl of 1 to 6 carbon atoms; or
R₁ and R₂ together is alkylene of 4 or 5 carbon atoms;
R₃=a free, esterified or etherified hydroxyl group; and
R₄=a free, esterified or etherified hydroxyl group.

2. A compound according to claim 1, wherein the 16-amino group is in the α-position.

3. A compound according to claim 1, wherein the 16-amino group is in the α-position and the 17-oxy group is in the β-position.

4. A compound according to claim 3, wherein R₃=hydroxy and R₄=hydroxy or methoxy.

5. Pharmaceutical composition having anti-arrhythmic properties, comprising a pharmaceutically effective amount of one or more of the compounds of claim 1 in admixture with a usual pharmaceutical carrier.

6. A compound selected from the group consisting of ent-16α-amino-3-methoxy-oestra-1,3,5(10)-trien-17β-ol and its hydrochloride, ent-16α-methylamino-3-methoxy-oestra-1,3,5(10)-trien-17β-ol and its hydrochloride, ent-16α-isopropylamino-3-methoxy-oestra-1,3,5(10)-trien-17β-ol and its hydrochloride, ent-16α-amino-oestra-1,3,5(10)-triene-3,17β-diol and its hydrochloride, ent-16α-methylamino-oestra-1,3,5(10)-triene-3,17β-diol and its hydrochloride, ent-16α-isopropylamino-oestra-1,3,5(10)-triene-3,17β-diol and its hydrochloride, ent-16α-amino-oestra-1,3,5(10)-triene-3,17β-diol maleate (1:1), ent-16α-methylamino-oestra-1,3,5(10)-3,17β-diol maleate (1:1), ent-16α-dimethylamino-3-methoxy-oestra-1,3,5(10)-trien-17β-ol and its hydrochloride, ent-16α-methylamino-3-methoxy-oestra-1,3,5(10)-trien-17α-ol and its maleate, ent-16β-methylamino-3-methoxy-oestra-1,3,5(10)-trien-17α-ol and its maleate, ent-16β-methylamino-oestra-1,3,5(10)-triene-3,17α-diol and its maleate, ent-16β-methylamino-3-methoxy-oestra-1,3,5(10)-trien-17β-ol and its maleate, ent-16β-methylamino-oestra-1,3,5(10)-triene-3,17β-diol and its maleate, ent-16β-amino-3-methoxy-oestra-1,3,5(10)-trien-17α-ol and its maleate, ent-16β-amino-oestra-1,3,5(10)-triene-3,17α-diol and its maleate, and ent-16β-amino-oestra-1,3,5(10)-triene-3,17β-diol and its maleate.

7. A compound according to claim 1 wherein R₁ is methyl.

8. A compound according to claim 1 wherein R₂ is methyl.

* * * * *